(12) United States Patent
Spohn et al.

(10) Patent No.: US 8,361,040 B2
(45) Date of Patent: Jan. 29, 2013

(54) FLUID PATH SET PROVIDING GRAVITY FLOW PREVENTION

(75) Inventors: Michael Spohn, Butler, PA (US); Thomas Cunningham, Mars, PA (US); Ronnie Mahofski, North Huntingdon, PA (US)

(73) Assignee: Medrad, Inc., Indianola, PA (US)

( * ) Notice: Subject to any disclaimer, the term of this patent is extended or adjusted under 35 U.S.C. 154(b) by 0 days.

(21) Appl. No.: 12/677,559

(22) PCT Filed: Sep. 15, 2008

(86) PCT No.: PCT/US2008/076378
§ 371 (c)(1),
(2), (4) Date: Mar. 11, 2010

(87) PCT Pub. No.: WO2009/036413
PCT Pub. Date: Mar. 19, 2009

(65) Prior Publication Data
US 2010/0204573 A1    Aug. 12, 2010

Related U.S. Application Data

(60) Provisional application No. 60/972,265, filed on Sep. 14, 2007.

(51) Int. Cl.
*A61M 25/00* (2006.01)
(52) U.S. Cl. .................. 604/264; 604/174; 604/250
(58) Field of Classification Search ............ 604/93.01, 604/250, 251, 258, 261, 264, 174, 179
See application file for complete search history.

(56) References Cited

U.S. PATENT DOCUMENTS

| | | | |
|---|---|---|---|
| 5,027,478 A * | 7/1991 | Suhr | 24/16 R |
| 5,309,604 A * | 5/1994 | Poulsen | 24/16 R |
| 5,460,609 A | 10/1995 | O'Donnell | |
| 5,573,515 A | 11/1996 | Wilson et al. | |
| 5,800,397 A | 9/1998 | Wilson et al. | |
| 6,074,374 A * | 6/2000 | Fulton | 604/249 |
| 6,187,529 B1 | 2/2001 | Fahy et al. | |
| 7,610,936 B2 | 11/2009 | Spohn et al. | |
| 2004/0122369 A1 | 6/2004 | Schriver et al. | |
| 2004/0254533 A1 | 12/2004 | Schriver et al. | |
| 2005/0234407 A1 | 10/2005 | Spohn et al. | |
| 2005/0234428 A1* | 10/2005 | Spohn et al. | 604/533 |
| 2007/0078401 A1* | 4/2007 | Servoss | 604/179 |
| 2007/0161970 A1 | 7/2007 | Spohn et al. | |

* cited by examiner

*Primary Examiner* — Bhisma Mehta
(74) *Attorney, Agent, or Firm* — Gregory L. Bradley; James R. Stevenson

(57) ABSTRACT

A fluid path for delivery of a fluid comprises first and second flexible tubes, each tube defining a transverse formation extending generally perpendicular to its longitudinal axis. Used to maintain the transverse formation in each tube, a clip mechanism includes a body comprising opposing flanges, each opposing flange defining at least a pair of recesses, each of the pair of recesses receiving one of the first and second flexible tubes, respectively, to define the respective transverse formations. The clip mechanism includes a support section connecting the opposing flanges such that the clip mechanism extends across the transverse formations and maintains their configuration. Due to the transverse formations, fluid contained within either tube at one end portion thereof cannot flow through the length thereof to displace a less dense fluid contained therein at the other end portion thereof under gravitational flow.

21 Claims, 5 Drawing Sheets

FLUID PATH SET PROVIDING GRAVITY FLOW PREVENTION

RELATED APPLICATIONS

This application is a 371 national phase application of PCT International Application No. PCT/US2008/076378, filed on Sep. 15, 2008 and designating the United States of America, which claims priority from U.S. Provisional Patent Application No. 60/972,265, filed Sep. 14, 2007, which is incorporated herein by reference in its entirety.

This application may contain subject matter that is related to that disclosed in the following co-pending U.S. patent application Ser. Nos. 11/931,594, filed Oct. 31, 2007 entitled "Flow Based Pressure Isolation and Fluid Delivery System Including Flow Based Pressure Isolation and Flow Initiating Mechanism"; application Ser. No. 11/551,027, filed Oct. 19, 2006 entitled "Fluid Delivery System, Fluid Path Set, and Pressure Isolation Mechanism with Hemodynamic Pressure Dampening Correction"; application Ser. No. 10/825,866, filed Apr. 16, 2004 entitled "Fluid Delivery System, Fluid Control Device, and Methods Associated with the Fluid Delivery System and Fluid Control Device"; application Ser. No. 10/818,477, filed Apr. 5, 2004 entitled "Fluid Injection Apparatus with Front Load Pressure Jacket, Light Illumination, and Syringe Sensing"; and application Ser. No. 10/326,582, filed Dec. 20, 2002 entitled "Front Load Pressure Jacket System with Syringe Holder and Light Illumination"; the disclosures of all the foregoing applications are incorporated herein by reference in their entireties.

BACKGROUND OF THE INVENTION

1. Field of the Invention

This invention is generally directed to the delivery of fluids in medical procedures and, more particularly, to apparatus, systems, and methods of preventing gravitational flow of contaminated or undesirable liquids to portions of a fluid delivery system intended from multiple uses.

2. Description of Related Art

In many medical diagnostic and therapeutic procedures, a medical practitioner such as a physician injects a patient with a fluid. In recent years, a number of injector-actuated syringes and powered injectors for pressurized injection of fluids, such as contrast media (often referred to simply as "contrast"), have been developed for use in procedures such as angiography, computed tomography, ultrasound, and NMR/MRI. In general, these powered injectors are designed to deliver a preset amount of contrast at a preset flow rate.

Angiography is used in the detection and treatment of abnormalities or restrictions in blood vessels. In an angiographic procedure, a radiographic image of a vascular structure is obtained through the use of a radiographic contrast which is injected through a catheter. The vascular structures in fluid connection with the vein or artery in which the contrast is injected are filled with contrast. X-rays passing through the region of interest are absorbed by the contrast, causing a radiographic outline or image of blood vessels containing the contrast. The resulting images can be displayed on, for example, a video monitor and recorded.

In a typical angiographic procedure, the medical practitioner places a cardiac catheter into a vein or artery. The catheter is connected to either a manual or to an automatic contrast injection mechanism. A typical manual contrast injection mechanism includes a syringe in fluid connection with a catheter connection. The fluid path also includes, for example, a source of contrast, a source of flushing fluid, typically saline, and a pressure transducer to measure patient blood pressure. In a typical system, the source of contrast is connected to the fluid path via a valve, for example, a three-way stopcock. The source of saline and the pressure transducer may also be connected to the fluid path via additional valves, again such as stopcocks. The operator of the manual contrast injection mechanism controls the syringe and each of the valves to draw saline or contrast into the syringe and to inject the contrast or saline into the patient through the catheter connection. The operator of the syringe may adjust the flow rate and volume of injection by altering the force applied to the plunger of the syringe. Thus, manual sources of fluid pressure and flow used in medical applications, such as syringes and manifolds, typically require operator effort that provides feedback of the fluid pressure/flow generated to the operator. The feedback is desirable, but the operator effort often leads to fatigue. Thus, fluid pressure and flow may vary depending on the operator's strength and technique.

Automatic contrast injection mechanisms typically include a syringe connected to a powered injector having, for example, a powered linear actuator. Typically, an operator enters settings into an electronic control system of the powered injector for a fixed volume of contrast and a fixed rate of injection. In many systems, there is no interactive control between the operator and the powered injector, except to start or stop the injection. A change in flow rate in such systems occurs by stopping the machine and resetting the injection parameters. Automation of angiographic procedures using powered injectors is discussed, for example, in U.S. Pat. Nos. 5,460,609; 5,573,515; and 5,800,397.

The pressure transducers used with automatic contrast injection mechanisms and manual contrast injection mechanisms used to conduct fluid injection procedures, such as angiographic and like procedures, are extremely sensitive to even moderate pressures generated during activation of the syringe, so the operator must typically close a valve to isolate the pressure transducer from the fluid path when the syringe is activated to prevent damage to the pressure transducer. Specifically, many pressure transducers can be damaged if they are subjected to pressures as low as about 75 psi. Because even a hand-held syringe can generate pressures of 200 psi or more, the isolation of the pressure transducer is essential in order to avoid pressure transducer failure. While the syringe is not activated, the valve is usually open to monitor patient blood pressure.

In a typical automatic contrast injection mechanism, the catheter is placed in fluid communication with the injection mechanism/fluid delivery system by a fluid path set that is often made up of a single patient disposable set ("SPDS") intended to be disposed of after a single use and a multi-use multi-patient disposable set ("MPDS") intended to be reused for a certain number of procedures or for a given period of time. The SPDS may be 52-65 inches in length, as an example, and is usually packaged in a straight configuration. This length is acceptable for a large majority of angiographic procedures, however, there is a certain percentage of procedures that need a longer length SPDS.

The length of the SPDS is often too long for medical technicians to easily hang or store. The longer length also presents handling issues to a manufacturer, including sterilization density concerns. Prior tubing sets have been manufactured in a coiled configuration, but such a configuration is not always desirable as the tubing takes a coiled set, which makes it difficult to handle during an angiographic injection procedure because the SPDS will re-coil and pull on the catheter.

The long length or straight (or "uncoiled") tubing in the SPDS also may present a gravitational flow situation in certain cases where blood present in the patient end of the SPDS may migrate up the tube set towards the MPDS when the SPDS is held in a vertical position. Such a vertical position is not typical during a procedure as the SPDS usually lies on the patient's legs in a horizontal position. In a small percentage of cases, medical technicians might not disconnect the SPDS form the MPDS after a procedure, but rather may let the SPDS hang down or hang up on an IV pole in a vertical position as they are taking care of the patient. This vertical position can cause a gravitational flow to initiate in the SPDS.

A gravitational flow is a fluid flow that takes place when two fluids of different densities come into contact. The denser or heavier fluid will seek to find the lowest position within a tube. If the heavier fluid is not at the lowest position, it will displace a less dense fluid and initiate a gravitational flow. This gravitational flow result can take place in several situations. In a first situation, gravitational flow can result when the SPDS tubing is left hanging down after a procedure. The higher density contrast fluid is located higher in the SPDS towards the MPDS and the lower density blood is located at the patient end of the SPDS. The denser contrast seeks to replace the lower density blood. This blood then flows up and into the MPDS contrast side if not caught in time by the user. The user at this point has to replace the contaminated MPDS. If not, blood or other contaminants in the MPDS could be injected through a new SPDS into the next patient.

A second exemplary situation can occur when a medical technician hangs the SPDS up on an IV pole after a procedure. The heavier density and blood contaminated contrast is at the patient end of the SPDS and the lighter density saline is located lower in the SPDS towards the MPDS. The denser, blood-contaminated contrast seeks to replace the lower density saline. This blood contaminated contrast then flows up and to the MPDS if not caught in time by the user. The user at this point has to again replace the contaminated MPDS.

SUMMARY OF THE INVENTION

Accordingly, there is a general need for a mechanism to be provided in a fluid tubing path set that prevents the above-mentioned gravitational flow of contaminated fluids from a single-use portion of a fluid tubing set and into a portion of the fluid tubing set or fluid dispensing apparatus intended for multiple uses. Such a fluid path set may be used for delivery of an injection fluid, and may further be provided as part of fluid delivery system. In one exemplary embodiment, the fluid delivery system may comprise a fluid injector associated with a first injectable fluid, a pressurizing device associated with a second injectable fluid, and the fluid path set for conveying the first injectable fluid and the second injectable to a patient. The fluid path set according to one embodiment generally comprises a flexible tube having a length defined between a first end and a second end of the flexible tube when the flexible tube is straightened and has a longitudinal axis extending along the length of the flexible tube. The flexible tube defines a transverse formation extending generally perpendicular to the longitudinal axis of the flexible tube. A clip mechanism is provided and maintains the transverse formation in the flexible tube. As a result of the transverse formation, fluid contained within the flexible tube at one end portion of the flexible tube cannot displace a less dense fluid contained within the flexible tube at the other end portion under gravitational flow.

The transverse formation may define any desired geometric configuration. One such formation is a loop, such as a generally circular loop. The loop includes two portions of the flexible tube, desirably extending in a side-by-side relationship. The clip mechanism may comprise recesses for receiving the two portions of flexible tube. One of the two portions of the flexible tube may be movably retained within one of the recesses such that a diameter of the loop is adjustable. A stop may be disposed on the flexible tube and be adapted to engage the clip mechanism so as to limit a range of adjustment of the loop.

The clip mechanism may comprise a body having recesses at each end thereof for receiving the two portions of the flexible tube at one end of the body and for receiving a third portion of the flexible tube opposing the two portions at the other end of the body such that a diameter of the loop is substantially fixed. The clip mechanism may comprise three recesses at each end thereof such that the clip mechanism is adapted to maintain loops defined by two co-extending flexible tubes.

The fluid path set may further comprise a second flexible tube having a length defined between a first end and a second end of the second flexible tube when the second flexible tube is straightened and has a longitudinal axis extending along the length of the second flexible tube. The second flexible tube desirably defines a second transverse formation extending generally perpendicular to the longitudinal axis of the second flexible tube. The clip mechanism maintains the second transverse formation in the second flexible tube, such that fluid contained within the second flexible tube at one end portion thereof cannot displace a less dense fluid contained within the flexible tube at the other end portion thereof under gravitational flow. The clip mechanism maintains the transverse formations in the first flexible tube and the second flexible tube may be a unitary clip mechanism that simultaneously engages the first flexible tube and the second flexible tube.

Another embodiment described herein relates to a method of operating a fluid delivery system. The method includes several steps including providing a fluid injector associated with a first injectable fluid, providing a pressurizing device associated with a second injectable fluid; and associating a fluid path set with the fluid injector and the pressurizing device for conveying the first injectable fluid and the second injectable to a patient. The fluid path set, as summarized above, generally comprises a flexible tube having a length defined between a first end and a second end of the flexible tube when the flexible tube is straightened and has a longitudinal axis extending along the length of the flexible tube. The flexible tube defines a transverse formation extending generally perpendicular to the longitudinal axis of the flexible tube. A clip mechanism is provided and maintains the transverse formation in the flexible tube. As a result of the transverse formation, fluid contained within the flexible tube at one end portion of the flexible tube cannot displace a less dense fluid contained within the flexible tube at the other end portion under gravitational flow. As further noted previously, the transverse formation may define a loop. At least a portion of the flexible tube may be movably associated with the clip mechanism and the method may comprise adjusting the diameter of the loop by manipulating the flexible tube. A stop may be disposed on the flexible tube and the method may comprise limiting a range of adjustment of the loop using the stop.

Further details and advantages will become clear upon reading the following detailed description in conjunction with the accompanying drawing figures, wherein like parts are identified with like reference numerals throughout.

DESCRIPTION OF THE PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and configurations. It is also to be understood that the specific devices illustrated in the accompanying drawing figures and described herein are simply exemplary and should not be considered as limiting.

Figure 1:
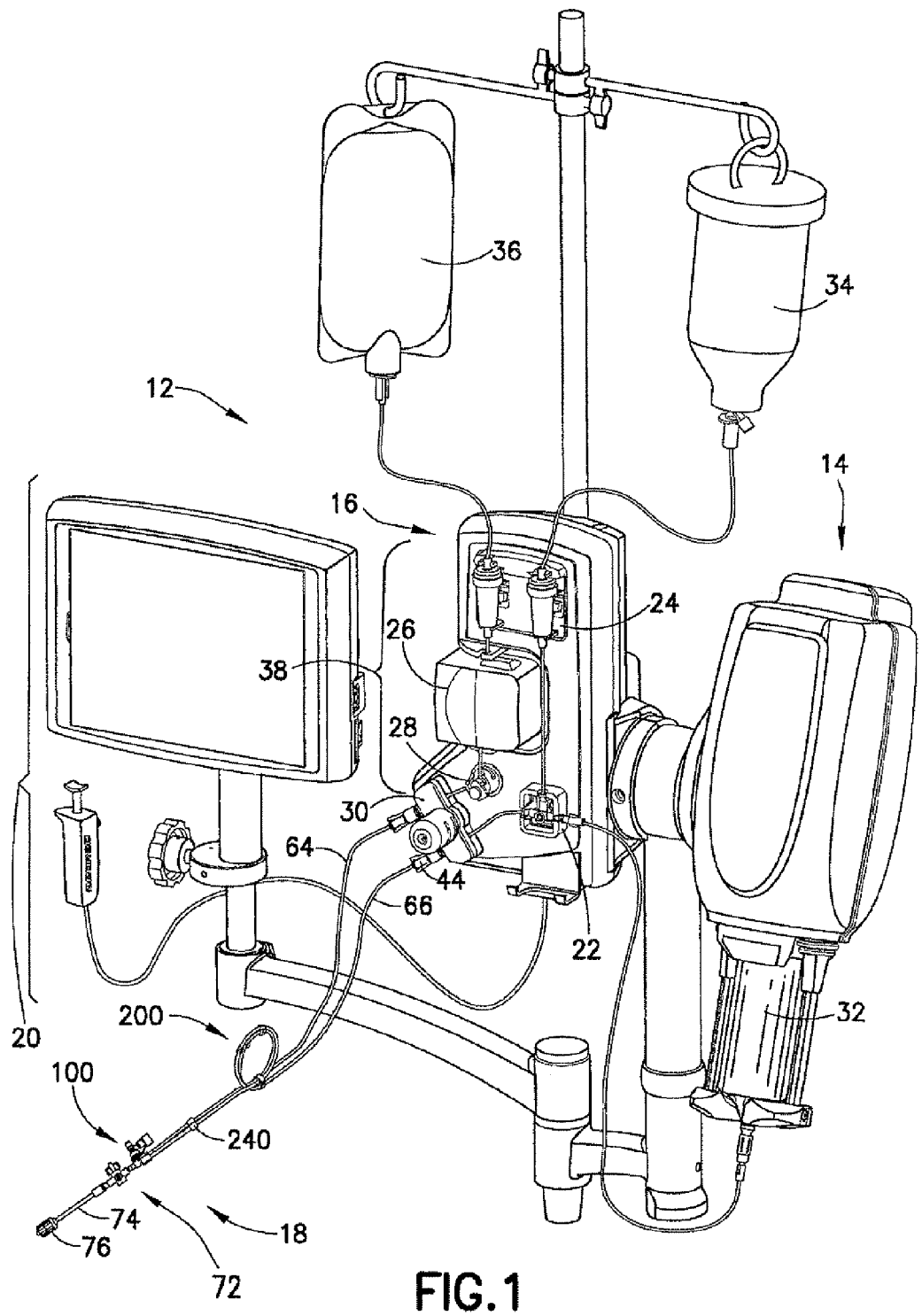
FIG. 1 is a perspective view of a fluid delivery system including a fluid path set incorporating gravity flow prevention techniques as described herein.

A fluid injector or delivery system 12 is illustrated generally in FIG. 1. Fluid delivery system 12 includes, generally, a fluid injector 14 operatively associated with a fluid control module 16. The details of fluid injector 14 are set forth in co-pending U.S. patent application Ser. No. 10/818,477, the disclosure of which was incorporated herein by reference previously. Fluid injector 14 is adapted to support and actuate a fluid delivery syringe, as described herein in connection with FIG. 2. A fluid control module 16 is associated with fluid injector 14 for controlling fluid flows delivered by the fluid injector 14. The details of fluid control module 16 are set forth in U.S. patent application Ser. No. 11/551,027, incorporated herein by reference previously. Fluid control module 16 is generally adapted to support and control a fluid path set 18 used to connect a syringe associated with fluid injector 14 to a catheter (not shown) to be associated with a patient. Fluid injector 14 and a syringe associated therewith serve as a pressurizing device for pressurizing fluid, such as contrast media ("contrast"), to be injected into a patient via the catheter. As an example, fluid injector 14 may be used as a vehicle to inject contrast at high fluid pressure into a blood vessel of a patient undergoing angiography. Additionally, fluid delivery system 12 includes a user-input control section or device 20 for interfacing with computer hardware/software (i.e., electronic memory) of fluid control module 16 and/or fluid injector 14, the details of which are identified in the foregoing Applications incorporated by reference. While the details of fluid control module 16 are set forth in detail in U.S. patent application Ser. No. 11/551,027, fluid control module 16 generally includes a housing unit supporting a valve actuator 22 for controlling a fluid control valve, such as a three-way stopcock, a fluid level sensing mechanism 24, a peristaltic pump 26, an automatic shut-off or pinch valve device 28, and an air detector assembly 30.

Figure 2:
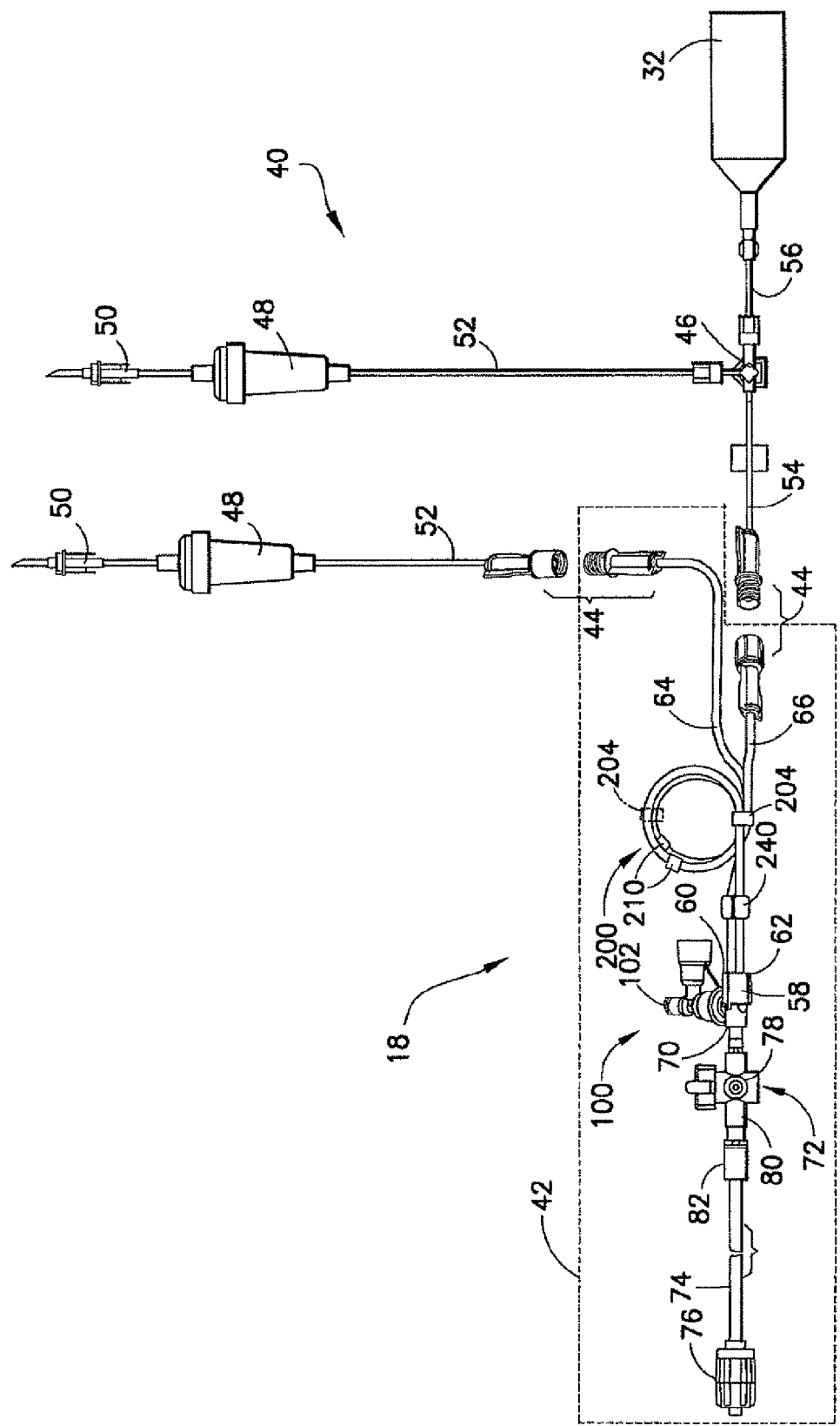
FIG. 2 is a side and partially perspective view of the complete fluid path set used in the fluid delivery system of FIG. 1.
Figure 3:
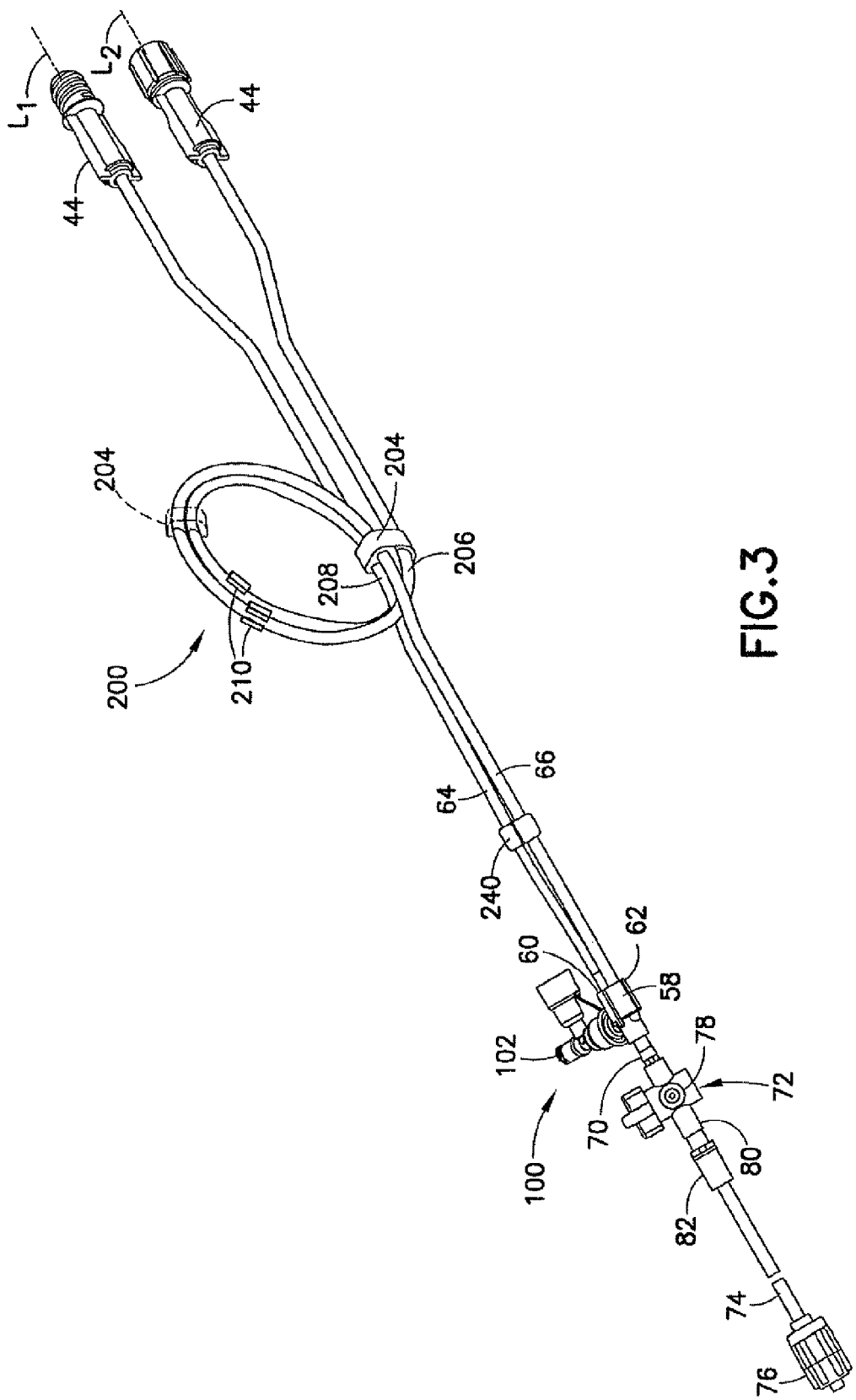
FIG. 3 is a perspective view of a portion of the fluid path set used in the fluid delivery system of FIG. 1 and which incorporates gravity flow prevention techniques.

Referring additionally to FIGS. 2-3, fluid control module 16 is generally adapted to support and control fluid flow through fluid path set 18 used to connect a syringe 32 associated with fluid injector 14 to a catheter (not shown) inserted in a patient. Fluid path set ("fluid path 18") may be considered to include syringe 32 that is associated with front-load fluid injector 14. Fluid path 18 is generally used to associate syringe 32 with a first or primary source of injection fluid 34, such as contrast, provided in a conventional medical container, which will be loaded into syringe 32 for a fluid injection procedure. First or primary fluid source 34 may be contrast in the case of angiographic or computed tomography procedures, as examples. Fluid path 18 is further adapted to associate syringe 32 with a secondary or additional source of fluid 36 also provided in a conventional medical container, which is to be supplied or delivered to the patient via the catheter. In a typical fluid delivery procedure, whether angiography or computed tomography, saline is often used as a secondary flushing fluid which is supplied to the patient between injections of contrast for clearing the catheter or clearing fluid path 18 of contrast, etc.

In a general fluid injection procedure involving fluid delivery system 12, fluid injector 14 is filled with fluid from primary fluid source 34 and delivers this fluid via fluid path 18 to the catheter and, ultimately, the patient. Fluid control module 16 generally controls or manages the delivery of the injection fluid through a control valve, such as a three-way stopcock, associated with fluid path 18 which is controlled or actuated by valve actuator 22 on the fluid control module 16. Fluid control module 16 is further adapted to deliver fluid from the secondary fluid source 36 under pressure via peristaltic pump 26 associated with the fluid control module 16. In a typical fluid injection procedure, valve actuator 22 actuates a valve, such as a three-way stopcock, associated with fluid path 18 which alternately permits fluid from the first or primary fluid source 34 to be loaded to syringe 32 associated with fluid injector 14 and then placed in a state to allow fluid communication or connection between syringe 32 and downstream portions of the fluid path 18 for delivering fluid such as contrast to the catheter connected to the fluid path 18.

Fluid path 18 is generally comprised of a first section or portion 40 and a second section or portion 42. First section 40 is generally adapted to connect syringe 32 to the primary fluid source 34 and the second section 42, and to connect the second section 42 to the secondary fluid source 36. First section 40 may be used as a multi-patient section or set disposed of after a preset number of fluid injection procedures are accomplished with fluid delivery system 12. Thus, first section 40 may be used for a preset number of fluid injection procedures involving one or more patients and may then be discarded. Optionally and less desirably, first section 40 may be adapted to be re-sterilized for reuse. First section 40 is provided as a sterile set typically in a sterile package. Second section 42 is intended as a per-patient section or set which is disposed of after each fluid injection procedure involving fluid delivery system 12. First section 40 and second section 42 are placed in fluid communication by use of one or more connectors 44, the details of which are set forth in U.S. patent application Ser. No. 11/551,027, previously incorporated by reference.

First section 40 includes a multi-position valve 46, such as a three-way stopcock valve, which is adapted to be automatically controlled or actuated by valve actuator 22 associated with fluid control module 16. In general, multi-position valve 46 may be actuated by valve actuator 22 to selectively isolate the syringe 32 and the primary fluid source 34 from the remainder of fluid path 18 and place the syringe 32 in fluid connection with the primary fluid source 34. This selectively allows fluid injector 14 to fill syringe 32 with fluid from primary fluid source 34, deliver fluid loaded into syringe 32 to fluid path 18 under pressure while isolating the primary fluid source 34, or isolate the syringe 32 and primary fluid source 34 from the remainder of the fluid path 18.

First section 40 includes intervening drip chambers 48 associated with the primary fluid source 34 and secondary fluid source 36. It is possible to replace drip chambers 48 with priming bulbs (not shown) in fluid path 18, if desired. Drip chambers 48 are adapted to be associated with the containers forming primary and secondary fluid sources 34, 36 with conventional spike members 50. Fluid level sensing mechanism 24 on fluid control module 16 is used to sense fluid levels in drip chambers 48 when fluid path 18 is associated with fluid injector 14 and fluid control module 16. Generally, operation of fluid delivery system 12 includes loading syringe 32 with fluid from the primary fluid source 34, which passes to the syringe 32 via the drip chamber 48 associated with the primary fluid source 34. Similarly, during operation of fluid delivery system 12 fluid, such as saline, from the secondary fluid source 36 is supplied to fluid path 18 via the drip chamber 48 associated with the secondary fluid source 36. Drip chambers 48 are generally adapted to permit fluid level sensors associated with fluid level sensing mechanism 24 to detect the level of fluid in the drip chambers 48, for example, by using optical or ultrasonic methods.

Respective output lines 52 made, for example, of conventional low pressure medical tubing, are associated with drip chambers 48 for connecting the drip chambers 48 to multi-position valve 46 and second section 42 of fluid path 18, respectively. An output line 54 from multi-position valve 46 connects the multi-position valve 46 and syringe 32 to second section 42 of fluid path 18 via connector 44. Due to the high injection pressures typically generated by fluid injector 14 during a fluid injection procedure such as angiography, output line 54 is desirably a high pressure medical tubing line. Additionally, a connecting tubing line 56 connecting multi-position valve 46 and syringe 32 is also desirably a high pressure medical tubing line to withstand these high fluid injection pressures.

A pressure isolation mechanism 100 is provided as part of fluid path 18 and the disposable second section 42 thereof in particular. Pressure isolation mechanism 100 serves several functions in fluid delivery system 12 but is primarily provided to connect a pressure transducer (not shown) to fluid path 18 so that hemodynamic blood pressure signal readings may be obtained during fluid delivery procedures involving fluid delivery system 12. This mechanism may serve as a physical merge point for the primary and secondary injection fluid paths, such as contrast and saline, for delivery to a patient during a fluid injection or delivery procedure via a catheter. Due to the need to protect the pressure transducer from damaging fluid pressure, which can occur at fluid pressure as low as about 75 psi and higher as indicated previously, pressure isolation mechanism 100 includes an internal valve structure that provides automatic overpressure protection for the pressure transducer during fluid delivery procedures, particularly those associated with the delivery of contrast at high pressure during angiographic procedures. Further details of pressure isolation mechanism 100 are provided in U.S. patent application Ser. No. 11/931,594, previously incorporated by reference.

Pressure isolation mechanism 100 is typically associated with second section 42 of fluid path 18 via a Y-T fitting 58 having two input ports 60, 62 respectively connected to input lines 64, 66. Y-T fitting 58 serves as the merge point for the primary and secondary injection fluid paths, such as contrast and saline, for delivery to a patient via a catheter during a fluid injection or delivery procedure. Input lines 64, 66 comprise a first input line 64 associated with the low pressure fluid delivery system 38 generally and output line 52 connected to drip chamber 48 associated with the secondary fluid source 36 in particular, and a second input line 66 associated with the high pressure system or device comprised by syringe 32 and fluid injector 14. This high pressure side of the fluid path 18 is alternately placeable in fluid communication with output line 52 connected to the drip chamber 48 associated with the primary fluid source 34 as described previously to fill syringe 32 with primary injection fluid, typically contrast. Both first input line 64 and the upstream output line 52 associated with secondary fluid source 36 are desirably high pressure medical tubing lines to avoid any damage to the first input line 64 and upstream output line 52 from high backpressure through the Y-T fitting 58. However, with the addition of a check valve in input port 60 of Y-T fitting 58, conventional low pressure medical tubing may be used for first input line 64 and upstream output line 52. Alternatively, first input line 64 could be made of high pressure medical tubing line and upstream output line 52 made of low pressure medical tubing with the addition of a check valve associated with the connector 44 used to connect first input line 64 to upstream output line 52 to isolate output line 52 from high backpressure through Y-T fitting 58. Similarly, second input line 66 is desirably formed of high pressure medical tubing and connects second input port 62 with output line 54 connected to multi-position valve 46 and, thereby, syringe 32. While Y-T fitting 58 is a convenient device to merge the primary and secondary fluid paths its presence in fluid path 18 is only exemplary and other merging arrangements, as discussed in U.S. patent application Ser. No. 11/931,594, previously incorporated by reference, may be used in place of Y-T fitting 58.

Y-T fitting 58 may further comprise a pressure transducer port 102 for associating the pressure isolation mechanism 100 with fitting 58, and an outlet port 70. A multi-position valve 72, such as three-way stopcock, is connected to outlet port 70 and may used as a simple shut-off valve to isolate the catheter (not shown) from fluid path 18. A catheter connection line 74 terminating in a luer connector 76 is associated with multi-position valve 72. One of the ports of the multi-position valve 72 may be a waste port 78 and the remaining port comprises an outlet port 80 that is configured with a luer connector 82 for associating catheter connection line 74 to multi-position valve 72 and, thus, fluid path 18.

Referring in particular to FIG. 3, the fluid path 18 includes a gravity flow prevention mechanism within the second section 42, in accordance with one embodiment of this disclosure. As shown, the first input line 64 is formed as a flexible tube having a first end (at connector 44) associated with the secondary fluid source 36 and a second end at input port 60 on Y-T fitting 58. The first input line 64 has a length defined between the first and second ends when the first input line 64 is straightened. A longitudinal central axis $L_1$ of the first input line 64 extends the length of the first input line 64. The first input line 64 is bent or formed to define a transverse formation 200 which may take any desirable form such as the loop formation shown in FIG. 3, and which extends generally perpendicular to the longitudinal axis $L_1$ of the first input line 64 in the illustrated configuration of the first input line 64. As shown, the transverse formation 200 defines a geometric configuration facing in a direction generally perpendicular to the longitudinal axis $L_1$ of the first input line 64 which is typically a circular or spiral loop, though it is to be appreciated that there are many different possible configurations for the transverse formation 200. For instance, the transverse formation 200 may be formed in an elliptical, trigonal, trapezoidal, parallelogrammatical, or other polygonal shape or, simply, the transverse formation 200 may be formed as a U-shaped bend defined by the first input line 64.

The transverse formation 200 is maintained in the desired transversely-extending configuration by a clip mechanism 204. Particularly, the clip mechanism 204 is associated with the first input line 64 such that when the first input line 64 is formed into a loop, with two adjacent portions 206, 208 of the first input line 64 extending or positioned in a side-by-side relationship. The clip 204 mechanism extends across both of the side-by-side portions 206, 208 and maintains spacing therebetween as well as fixing the orientation of the loop transverse formation 200 in this embodiment. The clip mechanism 204 includes orienting adjacent recesses for receiving the two adjacent portions 206, 208 of the first input line 64. Typically, one of the two adjacent portions 206, 208 (for example, portion 206) is desirably fixedly secured into one of the recesses defined by the clip mechanism 204 through a frictional fit or, if desired, the selected fixed portion 206, 208 may be fixed within the recesses through permanent connection such as by a chemical adhesive such as epoxy. The other portion 206, 208 (for example, portion 208) of the first input line 64 is desirably received within its corresponding recess in clip mechanism 204 in a looser fashion such that the diameter of the transverse formation 200 may be adjusted by pulling the "looser portion" 206, 208 of the first input line 64 through the recess in the clip mechanism 204 in either direction. A stop clip 210 is disposed on the circular loop 200 and is adapted to engage the body of the clip mechanism 204 so as to limit the range of adjustment of the circular loop 200.

As further shown in FIG. 3, the second input line 66 is also formed as a flexible tube having a first end (at connector 44) associated with the primary fluid source 34 and a second end at port 62 on Y-T fitting 58. The second input line 66 may be provided with clip mechanism 204 so that the second input line 66 may form a similar transverse formation 200 to that exhibited by the first input line 64 and the foregoing discussion related to the first input line 64 is equally applicable to the second input line 66 and is incorporate herein by reference. A longitudinal axis of the second input line 66 is designated with reference character $L_2$ in the accompanying Figures. Another feature shown in FIG. 3 concerning clip mechanism 204 is that clip mechanism 204 may be a unitary structure with two "left" side-by-side recesses associated with the adjacent portions 206, 208 of the first input line 64 and two "right" side-by-side recesses associated with the adjacent portions 206, 208 of the second input line 66. A second, identical clip mechanism 204 may be associated with the first and second input lines 64, 66 for stability and adjustment purposes. Likewise, a second stop clip 210 may be associated with the circular loop 200 defined by the second input line 66 in like manner to the first input line 64 described previously. The transverse formations 200 as circular loops are arranged side-by-side proximal to the Y-T fitting 58 in the single-patient/use section 42 of fluid path 18. However, it is to be appreciated that the loops 200, 200 may be formed side-by-side as shown or separately (e.g., staggered) along the longitudinal axes of the respective input lines 64, 66.

Accordingly, contamination of the first or multi-patient/use portion 40 of the fluid path set 18 due to gravitational flow of contaminated fluid contained within the second or single patient/use portion 42 of the fluid path 18 is prevented as any denser fluid contained within the second or single patient/use portion 42 of fluid path 18 must flow upward through the transverse formations 200 to reach the first or multi-patient/use portion 40 which is not possible. In particular, in one situation, this prevents upward contamination into the first or multi-patient/use portion 40 of the fluid path 18 when the second or single patient/use portion 42 is left hanging generally downward from the fluid control module 16 (or another structure) after use and higher density fluid, such as contrast, is located higher in the second or single patient/use portion 42 (such as in the first input line 64 and/or the second input line 66) and lower density fluid, such as blood, is located lower in the second or single patient/use portion 42 of the fluid path 18, such as in the catheter connection line 74. In this situation, the higher density contrast would normally replace the blood and the blood would displace upward and possibly intrude into the first or multi-patient/use portion 40. The presence of transverse formations 200 in the first and second input lines 64, 66 prevents any upward movement or migration of the blood into the first or multi-patient/use portion 40 as the heavier fluid would cannot flow upward against the force of gravity in the transverse formations 200 to displace the lower-level located blood. Likewise, contamination of the multi-patient/use portion 40 of the fluid path 18 is also prevented when the fluid path 18 is left hanging upward from an IV pole or another structure or even the fluid control module 16, with the second or single patient/use portion 42 pointing generally upward. In this situation, the heavier, denser, contaminated contrast fluid/blood mixture is typically contained within the fluid path 18 at the patient end of the second or single patient/use portion 42 of the fluid path 18, such as in the catheter connection line 74, and lower density saline is located lower in the second or single patient/use portion 42, such as in the first and/or second fluid lines 64, 66. The interposing of transverse formations/circular loops 200 prevents the heavier fluid from migrating downward and displacing the less dense saline and possibly entering the multi-patient/use portion 40.

As previously discussed, the transverse formations 200 defined as loops by the first and second input lines 64, 66 are adjustable. This allows for adjustment in the overall length of the second portion 42 of the fluid path 18 in an exemplary range from about 52 inches to about 65 inches. The transverse formations 200 define smaller diameters to approximately 2 inches when the length of the second portion is 65 inches. The transverse formations 200 can be larger or smaller than 6 inches so as to optimize packaging density. As noted previously, stops 210 are incorporated into the transverse formations 200 to limit adjustments of the transverse formations 200 to between maximum and minimum sizes. Defining a minimum diameter of the transverse formations 200 helps to prevent a tube kink if the transverse formations 200 are drawn in too tightly. Packaging lengths can be minimized by packaging the transverse formations 200 with a large diameter. For instance, the transverse formations 200 could be packaged to be approximately 19 inches in diameter. However, if the transverse formations 200 are packaged with too large a diameter they will tend to become set and return to a coiled configuration during use. Thus, in order to maximize diameter and minimize packaging length, an adhesive tape or alligator clip may be provided to secure the first and second input lines 64, 66 to a sterile drape or a similar structure in order to retain these tubes in a generally straight configuration.

Figure 4:
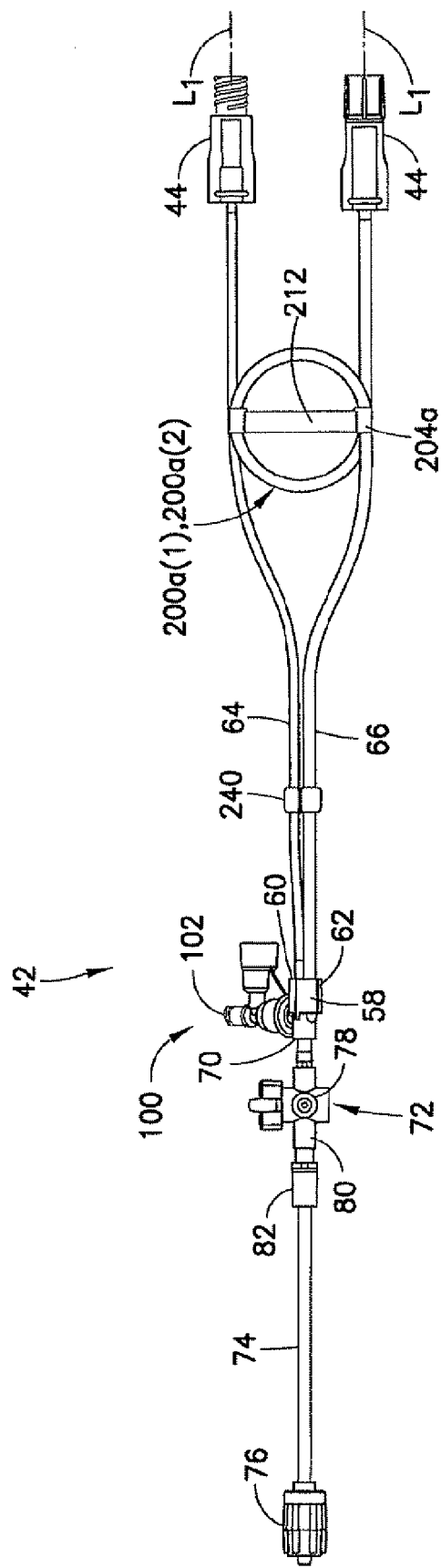
FIG. 4 is a side view of a portion of a fluid of the fluid path set used in the fluid delivery system of FIG. 1 and which incorporates gravity flow prevention techniques according to another embodiment.
Figure 5:
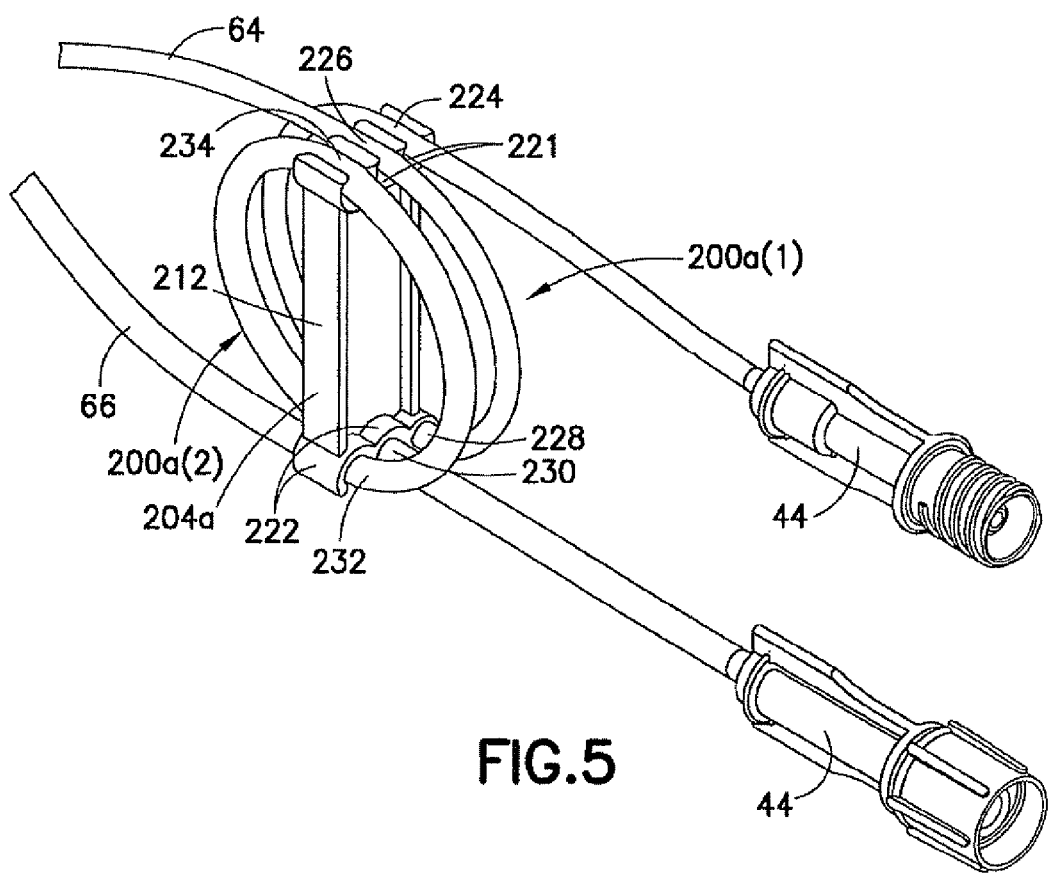
FIG. 5 is a perspective view of a portion of the fluid path set illustrated in FIG. 4.
Figure 6:
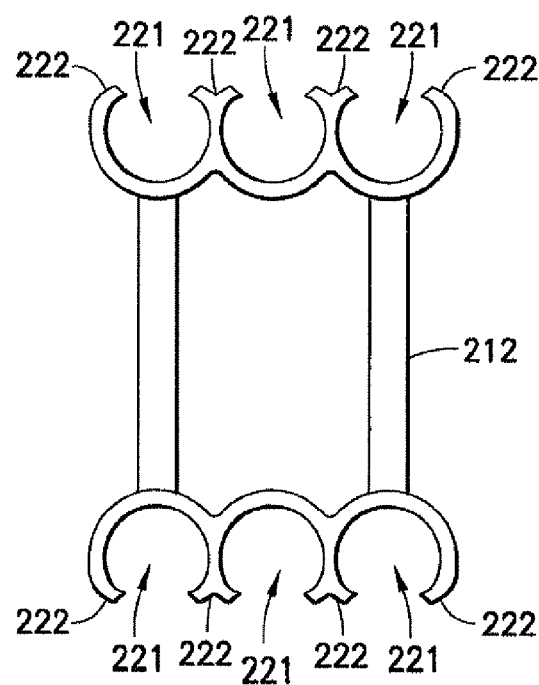
FIG. 6 is a front view of an adjustment clip incorporated into the gravity flow preventing fluid path set of FIG. 5.

Referring to FIGS. 4-6, another embodiment is shown. In this embodiment, the opposing clip mechanisms 204 shown in FIG. 3 are integrated into a singular clip mechanism 204a. Clip mechanism 204a further exhibits a separating support section 212 between the top and bottom ends of the clip mechanism 204a. As shown, transverse formations 200a(1), 200a(2) are defined when the first and second input lines 64, 66 are respectively associated with clip mechanism 204a. The loop transverse formations 200a(1), 200a(2) are arranged side-by-side in generally similar manner to previous embodiments and are maintained in the side-by-side, loop configuration by unitary clip mechanism 204a, which simultaneously engages both the first input line 64 and the second input line 66. As shown in FIG. 6, the unitary clip mechanism 204a includes a body defining three recesses 221 at each end of the body. Opposing flanges 222 are provided to secure a single portion of the first and second input lines 64, 66 with a single respective recess 221. As shown in FIG. 5, two side-by-side portions 224, 226 of the first input line 64 are disposed within two of the three recesses 221 at the upper end of the clip mechanism 204a while one portion 228 of the first input line 64 is disposed within one of the three recesses 221 at the lower end of the clip mechanism 204a. In like manner, two side-by-side portions 230, 232 of the second input line 66 are disposed within two of the three recesses 221 at the lower end of the clip mechanism 204a while a one portion 234 of the second input line 66 is disposed within the remaining top recess 221 at the upper end of the clip mechanism 204a. Since the unitary clip mechanism 204a extends across and defines the diameter of both circular loops 200a, the diameters of the transverse formations 200a are fixed and cannot be adjusted. As shown, the transverse formations 200a(1), 200a(2) are defined proximate to the first ends of the first and second input lines 64, 66. However, the loop transverse formations 200a(1), 200a(2) may be defined at any point along the lengths of the flexible tubes forming the first and second input lines 64, 66. Additionally, a distal tube connector 240 may be provided to secure the first and second input line 64, 66 together at a point proximal to the Y-T fitting 58. The purpose and operation of the transverse formations 200a(1), 200a(2) is identical to that described previously in this disclosure and not repeated here for brevity.

While transverse formations 200, 200a are described as being in the form of a flexible tube formed into a loop this should not be considered limiting. The transverse formations 200, 200a may be any structure (flexible or rigid) in the fluid path of the first and second input lines 64, 66 which forms a perpendicular or transverse structure that will prohibit the replacement under gravity flow conditions of a heavier fluid for a lighter (e.g., less dense) fluid. Such a transverse structure (flexible or rigid) may even be incorporated into a fluid control device present in the fluid path such as a valve and the like. It is also to be appreciated that the transverse formations 200, 200a described herein may incorporate both flexible and rigid sections or portions of tubing. For instance, transverse formations 200, 200a may be formed of rigid tubing structures connected between separate sections of tubing forming the first and second input lines 64, 66, described above. Transverse formations 200, 200a are terms intended to encompass each of the foregoing alternatives.

While several embodiments of a fluid path set providing gravity flow prevention and methods associated therewith were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A fluid path set for delivery of an injection fluid, comprising:
    (a) a first flexible tube having a length defined between a first end portion and a second end portion thereof when straightened and having a longitudinal axis extending the length thereof;
    (b) a second flexible tube having a length defined between a first end portion and a second end portion thereof when straightened and having a longitudinal axis extending the length thereof, the first flexible tube and the second flexible tube each defining a transverse formation extending generally perpendicular to the longitudinal axis corresponding thereto; and
    (c) a clip mechanism for maintaining the transverse formation in each of the first flexible tube and the second flexible tube, comprising a clip body comprising opposing flanges, each opposing flange defining at least a pair of recesses, each of the pair of recesses receiving one of the first flexible tube and the second flexible tube, respectively, to define the respective transverse formations, and a separating support section connecting the opposing flanges such that the clip mechanism extends across the transverse formations and maintains a configuration of the respective transverse formations;
    whereby, due to the respective transverse formations, a fluid contained within either of the first flexible tube or the second flexible tube at the one end portion thereof cannot flow through the length of the first flexible tube or the second flexible tube to displace a less dense fluid contained within the first flexible tube or the second flexible tube at the other end portion thereof under gravitational flow.

2. The fluid path set according to claim 1, wherein the configuration of the respective transverse formations defines a geometric configuration.

3. The fluid path set according to claim 2, wherein the geometric configuration is a loop.

4. The fluid path set according to claim 3, wherein the opposing flanges define three recesses.

5. The fluid path set according to claim 1, wherein the first flexible tube and the second flexible tube extend in a side-by-side relationship through the respective pair of recesses.

6. The fluid path set according to claim 1, wherein the first flexible tube and the second flexible tube are movably retained within the respective pair of recesses.

7. The fluid path set according to claim 1, wherein the clip body comprises one of the opposing flanges defining a third recess for receiving a portion of one of the first flexible tube and the second flexible tube.

8. The fluid path set according to claim 1, wherein the clip body is unitary.

9. A fluid delivery system, comprising:
    (a) a fluid injector associated with a first injectable fluid;
    (b) a pressurizing device associated with a second injectable fluid; and
    (c) a fluid path set for conveying the first injectable fluid and the second injectable fluid to a patient and comprising:
        (I) a first flexible tube having a length defined between a first end portion and a second end portion thereof when straightened and having a longitudinal axis extending the length thereof;
        (II) a second flexible tube having a length defined between a first end portion and a second end portion thereof when straightened and having a longitudinal axis extending the length thereof, the first flexible tube and the second flexible tube each defining a transverse formation extending generally perpendicular to the longitudinal axis corresponding thereto; and (III) a clip mechanism for maintaining the transverse formation in each of the first flexible tube and the second flexible tube, comprising a clip body comprising opposing flanges, each opposing flange defining at least a pair of recesses, each of the pair of recesses receiving one of the first flexible tube and the second flexible tube, respectively, to define respective transverse formations, and a separating support section connecting the opposing flanges such that the clip mechanism extends across the transverse formations to maintain the configuration of the respective transverse formations;

whereby, due to the transverse formations, a fluid contained within either of the first flexible tube or the second flexible tube at the one end portion thereof cannot flow through the length of the first flexible tube or the second flexible tube to displace a less dense fluid contained within the first flexible tube or the second flexible tube at the other end portion thereof under gravitational flow.

10. The fluid delivery system according to claim 9, wherein the configuration of the respective transverse formations defines a geometric configuration.

11. The fluid delivery system according to claim 10, wherein the geometric configuration is a loop.

12. The fluid delivery system according to claim 9, wherein the first flexible tube and the second flexible tube extend in a side-by-side relationship through the respective pair of recesses.

13. The fluid delivery system according to claim 9, wherein the first flexible tube and the second flexible tube are movably retained within the respective pair of recesses.

14. The fluid delivery system according to claim 9, wherein the clip body comprises one of the opposing flanges defining a third recess for receiving a portion of one of the first flexible tube and the second flexible tube.

15. The fluid delivery system according to claim 9, wherein the opposing flanges define three recesses.

16. A single-use fluid path set for delivery of at least one of a first fluid and a second fluid into a patient, comprising:

a first flexible tube having a length defined between a first end portion and a second end portion thereof when straightened and having a longitudinal axis extending the length thereof;

a second flexible tube having a length defined between a first end portion and a second end portion thereof when straightened and having a longitudinal axis extending the length thereof, the first flexible tube and the second flexible tube each defining a transverse formation extending generally perpendicular to the longitudinal axis corresponding thereto;

a clip mechanism for maintaining the transverse formation in each of the first flexible tube and the second flexible tube, comprising a clip body comprising opposing flanges, each opposing flange defining at least a pair of recesses, each of the pair of recesses receiving one of the first flexible tube and the second flexible tube, respectively, to define the respective transverse formations, and a separating support section connecting the opposing flanges such that the clip mechanism extends across the transverse formations to maintain the configuration of the respective transverse formations;

connector fittings connected to the first end portion of the first flexible tube and second flexible tube, respectively; and a fitting having a first inlet port connected to the second end portion of the first flexible tube, a second inlet port connecting to the second end portion of the second flexible tube, and an outlet port for connecting to an outlet line in communication with the patient, thereby enabling the fitting to communicate the at least one of the first fluid and the second fluid to the patient; and whereby, due to the respective transverse formations, a fluid contained within either of the first flexible tube or the second flexible tube at the one end portion thereof cannot flow through the length of the first flexible tube or second flexible tube to displace a less dense fluid contained within the first flexible tube or the second flexible tube at the other end portion thereof under gravitational flow.

17. The single-use fluid path set according to claim 16, wherein each of the respective transverse formations defines a respective loop.

18. The single-use fluid path set according to claim 16, wherein the first flexible tube and the second flexible tube extend in a side-by-side relationship through the respective pair of recesses.

19. The single-use fluid path set according to claim 16, wherein the first flexible tube and the second flexible tube are movably retained within the respective pair of recesses.

20. The single-use fluid path set according to claim 16, wherein the clip body comprises one of the opposing flanges defining a third recess for receiving a portion of one of the first flexible tube and the second flexible tube.

21. The single-use fluid path set according to claim 16, wherein the clip body comprises three recesses in each of the opposing flanges.

* * * * *